United States Patent [19]

Murphy et al.

[11] 4,358,623

[45] Nov. 9, 1982

[54] PROCESS FOR CATALYTICALLY CONVERTING METHANOL TO FORMALDEHYDE

[75] Inventors: Carl D. Murphy; William P. McMillan, both of Corpus Christi, Tex.

[73] Assignee: Celanese Corporation, New York, N.Y.

[21] Appl. No.: 286,235

[22] Filed: Jul. 23, 1981

[51] Int. Cl.$^3$ .................... C07C 47/052; C07C 47/055
[52] U.S. Cl. .................................... 568/473; 568/474; 568/472; 568/471
[58] Field of Search ................ 568/473, 474, 471, 472

[56] References Cited

U.S. PATENT DOCUMENTS

| | | | |
|---|---|---|---|
| 1,968,552 | 7/1934 | Bond et al. | 568/472 |
| 2,462,413 | 2/1949 | Meath | 568/473 |
| 2,504,402 | 4/1950 | Field | 568/473 |
| 2,908,715 | 10/1959 | Eguchi | 568/473 |
| 3,959,383 | 5/1976 | Northeimer et al. | 568/473 |
| 4,029,636 | 6/1977 | Lowry et al. | 568/474 |
| 4,097,535 | 6/1978 | Yang et al. | 568/473 |

FOREIGN PATENT DOCUMENTS 1131380  10/1968  United Kingdom ................ 568/473

OTHER PUBLICATIONS

Bergles, "Enhancement of Heat Transfer," vol. 6, 6th Int. Heat Transfer Conference, pp. 89–108, Pub Hemisphere Pub. Co. (1978).
Calderbank et al., "Trans. Inst. of Chem. Engrs." vol. 35, pp. 195–207 (1957).
Schluender, "Chem. Reaction Eng'g. Reviews—Houston", ACS Symp. Series 72 (1978).
Kirk-Othmer, "Ency. of Chem. Tech.", vol. 11, Third ed. p. 233, John Wiley & Sons.

Primary Examiner—Werren B. Lone
Attorney, Agent, or Firm—R. M. Pritchett

[57] ABSTRACT

In catalytically oxidizing methanol in the vapor phase according to already-known processes for the production of formaldehyde, the hot formaldehyde-containing gaseous effluent of the catalytic converter is rapidly cooled by being passed through the tubes of a heat exchanger which are filled with balls composed of a solid which is substantially inert toward formaldehyde. As compared with a similar cooling system in which the tubes are empty or in which enhancement of heat transfer is attempted by using metal heat-transfer enhancement devices such as twisted metal ribbons, the present method affords reduced post-reaction decomposition of formaldehyde while at the same time allowing use of a relatively high temperature on the shell side of the heat exchanger whereby it becomes possible to raise steam at a pressure higher than that characteristic of the prior art.

6 Claims, No Drawings

PROCESS FOR CATALYTICALLY CONVERTING METHANOL TO FORMALDEHYDE

BACKGROUND OF THE INVENTION

This invention relates to the catalytic oxidation of methanol in the vapor phase to produce formaldehyde. More particularly it relates to a method for enhancing the effectiveness of the cooling step which follows the catalytic oxidation and in which the hot gases being discharged from the catalytic converter are cooled down to a temperature at or below which said gases can then be further processed to recover the contained formaldehyde by methods already known to those experienced in the art.

Many processes are known for catalytically oxidizing methanol vapor to formaldehyde, differing from one another in the number of reaction stages employed, in the nature of the catalyst, and in the ratio of oxygen to methanol in the reactant gases entering the catalytic conversion system. (Some processes employ a high oxygen:methanol ratio whereby a substantially complete conversion is obtained per reaction pass, while others employ a lower ratio of oxygen to methanol whereby a substantial portion of the methanol is not reacted and is subsequently recycled to the catalytic converter.) In some of the processes the reaction is conducted in a single stage while in others there are two reaction stages in sequence with the gases leaving the first stage being cooled and, if desired, modified as to their composition before being introduced into the second stage. Various catalyst are known, including silver gauze, silver crystals, silver on a suitable inert support, and several compositions comprising the oxides of various metals. The several processes vary among themselves also in that some of the catalysts are thought of as being essentially oxidation catalysts whereas others, including especially the more highly active metallic silver catalysts, are considered to catalyze both the oxidation and the dehydrogenation of the methanol.

Representative of the current oxidation technology is U.S. Pat. No. 3,959,383 to Northeimer, which describes the use of two reaction stages in sequence. Both stages use a silver catalyst, with the second stage catalyst being specifically silver crystals. The hot gaseous effluent from the first stage is cooled, and its composition adjusted before it is passed on to the second stage. The effluent from the second stage is then cooled again, and the cooled gases enter an absorption system for recovery of the contained formaldehyde by conventional methods. U.S. Pat. No. 2,462,413, to Meath, describes a process similar to that of Northeimer except that the catalyst is used on a support. U.S. Pat. No. 1,968,552, to Bond et al., describes a single-stage process using silver crystals. U.S. Pat. No. 2,504,402, to Field, describes a multiple-stage conversion system in which various catalysts can be employed, with iron-promoted molybdenum oxide being specifically exemplified.

The foregoing are but a sampling of the voluminous literature dealing with the catalytic conversion of methanol to formaldehyde, but it is to be understood that the present invention, to be discussed more fully below, has to do with the handling of the hot effluent gases from the catalytic converter and not with the mode of operation of the converter, nor with the catalyst or catalysts employed therein.

Regardless of variations in such factors as type of catalyst, number of reaction stages, and reactant proportions, all of the several reaction systems are operated with recognition of the fact that formaldehyde contained in the hot reaction product gases is subject to rapid post-reaction decomposition so long as the gases are hot (although the problem is less severe with the metal oxide catalyst, which operate at comparatively low temperatures). It is therefore standard practice to employ any of several expedients to reduce the temperature of the hot gases as rapidly as possible. For example, U.S. Pat. No. 2,908,715, to Eguchi et al., describes spraying water, methanol, or aqueous formalin directly onto the under surface of the catalyst layer in order to quench the hot gases as quickly as possible. Other variants of this spray-quench technique are also employed in which, although the liquid is not sprayed directly against the catalyst, it is still sprayed into the reaction chamber as close as possible to the downstream side of the catalyst. Other approaches include the use of ordinary shell-and-tube aftercoolers positioned as closely as possible to the catalyst bed as exemplified in British Pat. No. 1,131,380, to Farbenfabriken Bayer, in which the heart of the invention is the cooling of the reactor effluent gas to a temperature below 100° C. in a time of less than 0.1 second. This is accomplished by keeping the zone between catalyst and catalyst condenser extremely small in volume. While not specifically disclosed in British Pat. No. 1,131,380, one feasible approach to minimizing the retention time of the hot gases between the catalyst and the condenser is to have the catalyst actually positioned on top of the tube sheet of the condenser or aftercooler, separated therefrom only by a spacer which prevents actual contact between the catalyst and the tube sheet of the condenser.

To recapitulate, it is well-known in the art to minimize the retention time of the hot reactor effluent gases between the catalyst and the aftercooler or condenser in order to lower the gas temperature as rapidly as possible. The present invention is not directed to the broad idea of effecting this rapid cooling but, rather, to a particularly efficacious method for doing so.

As will be seen, this invention deals primarily with a method for enhancing the heat-transfer characteristics of the aftercooler which follows the methanol-oxidation catalytic converter, the method comprising the use of a certain type of insert in the tubes of the aftercooler in order to bring about the desired heat transfer enhancement.

The use of inerts to enhance heat transfer is not in itself new. For example, a good over-all discussion is presented by A. E. Bergles in a paper titled "Enhancement of Heat Transfer" published in Vol. 6 of the Sixth International Heat Transfer Conference, pages 89–108, published by Hemisphere Publishing Corp., Wash. D.C., in 1978. There are also studies of heat transfer within packed beds of solids contained in tubes as exemplified by Calderbank et al., "Transactions of the Institution of Chemical Engineers" Volume 35 pages 195–207 (1957). Another treatment of the subject is provided by Schluender in Chapter 4 of "Chemical Reaction Engineering Reviews—Houston," ACS Symposium Series 72 (1978), which, like Calderbank et al., is concerned largely with catalytic reaction systems and the like rather than with the employment of tube inserts for the specific purpose of enhancing heat transfer. Finally, another system involving heat transfer in packed tubes is disclosed in U.S. Pat. No. 4,029,636, to Lowry et al., in which a hot gas containing molybdenum trioxide is passed through cooled tubes which are packed with ceramic balls in order to condense the molybdenum trioxide onto the surface of the balls so that it is removed from the gases and does not contaminate downstream processing equipment. The object is not to enhance the heat transfer rate but simply to condense out the molybdenum trioxide. No effort is made to provide rapid cooling of the gases as an end in itself, and enhancing the heat transfer as such is not taught by the patentees. Temperatures are quite high, even downstream from the cooled ceramic balls.

Although the enhancement of heat transfer by the use of inserts in the tubes of tube-and-shell heat exchangers is not new as explained above, it is not believed that this has ever been successfully attempted in cooling the gaseous effluent from a methanol-oxidation reactor. One reason is probably that metal inserts such as twisted metal ribbons that are known for heat transfer enhancement will also tend to catalyze the decomposition of hot formaldehyde vapor. This decomposition is discussed in, for example, the Kirk-Othmer "Encyclopedia of Chemical Technology" on page 233 of Volume 11 of the Third edition (1980) published by John Wiley & Sons. Chromia and alumina are mentioned in the same reference as being catalysts for the formaldehyde decomposition, and the alumina, as a known decomposition catalyst, would also cast a shadow on the idea of using non-metallic inserts for the same purpose. Broadly speaking, it appears that the art to date has considered, if it has considered at all the idea of using enhanced heat transfer for this purpose, that the combination of relatively high inlet temperatures along with adverse catalytic effects of the surfaces of whatever tube inserts might be employed, leads to an undesirable degree of formaldehyde decomposition. The result has been that the art heretofore has opted for either a direct quench using a cold liquid spray or, alternatively, empty cooling tubes made of a high alloy metal and cooled by a relatively low temperature liquid on the shell side.

One additional factor relating to the employment of enhanced heat transfer devices as contemplated by the prior art is that it has not generally been recognized that a high degree of heat transfer enhancement can actually be attained without, at the same time, suffering a significant pressure drop in the gas or other fluid passing through the tubes containing the heat transfer enhancement devices. For example, twisted metal ribbons, which do not normally cause a serious pressure drop problem, do not effect a very great improvement in heat transfer in the tubes in which they are installed. At the same time, packing the tubes with small solid bodies such as beads can result in a substantial obstruction to gas flow with resulting increase in pressure drop. Yet, in cooling the effluent gas from a methanol converter, it is not only necessary to effect rapid cooling for reasons of chemical efficiency but it is also necessary to avoid gas pressure drop as much as possible, because the converter itself is operated at low pressure (of the order of about 0.3–0.6 atmosphere gauge).

It is an object of the present invention to provide a method for rapidly cooling the effluent gas from a catalytic converter in which methanol is being converted to formaldehyde in the presence of molecular oxygen. It is another object to provide a method for effecting such cooling without the process complications inherent in the use of an internal liquid coolant. It is another object to cool the converter effluent gases more rapidly than in an ordinary shell-and-tube condenser or aftercooler of conventional design, with the result that post-reaction decomposition of the formaldehyde contained in the hot converter effluent gases, including a reversion reaction in which formaldehyde and hydrogen react to form methanol, is less than that which is experienced when using an ordinary shell-and-tube aftercooler. Other objects will be apparent from the following detailed description and examples.

BRIEF SUMMARY OF THE INVENTION

In accordance with the present invention, the hot formaldehyde-containing gases issuing from the methanol converter in an otherwise conventinal reaction system in which methanol is being reacted with molecular oxygen in the pressence of a catalyst to convert the methanol to formaldheyde is passed through an array of externally-cooled tubes (e.g., the tubes in a shell-and-tube heat exchanger) which are packed with inert balls, typically and preferably made of a ceramic, such as an aluminosilicate, the balls being relatively large in comparison with the inside diameter of the tubes. The resulting heat transfer characteristics of the ball-packed heat exchanger (or reactor aftercoler) are such that post-reaction decomposition of the formaldehyde contained in the converter effluent gas is less than that experienced in an otherwise similar heat exchanger the tubes of which are not packed with the balls. Performance of the ball-packed heat exchanger is also superior, as indicated by reduction in formaldehyde decomposition, to that of an exchanger the tubes of which contain metallic heat-transfer enhancement devices such as twisted metal ribbons. At the same time, pressure drop through the tubes containing the balls is significantly less than that experienced with tubes packed with beads (i.e., balls of a very small size).

In addition to reducing post-reaction decomposition of the formaldehyde, use of the present invention also facilitates maintaining a relatively high temperature in the liquid (normally water) which is circulated through the shell side of the aftercooler, because the heat transfer is enhanced to such a degree that the desired rate of cooling can be maintained even with a somewhat higher than customary temperature on the shell side of the cooled tubes. This makes possible an additonal benefit in that if the hot water exiting from the aftercooler shell is allowed to flash into steam (a common industrial practice carried out for the purpose of utilizing the heat as process steam), the steam which is so produced from the present improved process can be appreaciably higher in pressure than normally characteristic of the prior art. As will be understood, of course, the value, and the process utility, of steam is higher at higher pressures than at lower pressures.

Finally, of course, the presently-obtained heat transfer enhancement makes possible a reduction in the heat transfer surface of the reaction aftercooler as compared with the prior art.

DETAILED DESCRIPTION OF THE INVENTION

As has been explained previously, the nature of the catalytic methanol-oxidation system supplying the hot converter effluent gases to be cooled by the present improved method is of no significance except that, as previously explained, the post-reaction decomposition problem is less severe with systems using metal oxide catalysts than with those using silver catalysts. Whatever the source of the hot gases (e.g., single-stage catalyst systems as compared with two-stage systems, or silver-based catalysts as compared with metal oxide catalysts) the problem of formaldehyde decomposition immediately following the reaction step constitutes a generally-experienced process difficulty. The decomposition is also a problem in low-conversion methanol oxidation systems (those using insufficient air for complete reaction of the methanol) just as it is in those systems in which the ratio of air (or oxygen) to methanol in the reaction system is high enough that complete, or nearly complete, conversion of the methanol therein is effected. It will be readily understood that in any case the hot converter effluent gases contain gaseous formaldehyde, and that its decomposition rate is related to its temperature. Reactor effluent temperature, by which is meant the temperature of gases leaving the downstream side of the last catalyst in the converter before contact with the cooling device even though the cooling device might be actually located within the converter case, are generally in the range of about 290° C. to 700° C. Pressure within the converter, and therefore the pressure of the gases leaving the converter, is very slightly above atmospheric—i.e., approximately 0.3–0.6 atmosphere gauge.

As explained above, it is established practice in this art to cool the gases as rapidly as possible as soon as they have passed through the catalyst, and this commonly entails, among other measures, minimizing to the greatest extent feasible the time interval between the disengagement of the hot gases from the downstream face of the catalyst and their entry into whatever post-reaction cooling device is to be employed.

One effective approach to this problem of minimizing the time interval during which the reaction gases are hot—and this is recommended in the practice of the present invention—is to position the shell-and-tube reaction aftercooler substantially vertically, with the methanol-oxidation catalyst being mounted immediately atop its upper tube sheet and separated from the tube sheet and the entrances to the tubes only by a shallow support grating or other highly gas-permeable catalyst support means in order to ensure complete utilization of the catalyst. That is, if the catalyst were resting directly on the aftercooler tube sheet, not only would the relatively cold metal of the tube sheet lower the catalyst temperature excessively, but gases passing through the catalyst would also tend to channel through those parts of the catalyst which were immediately above tube openings while being directed away from those parts of the catalyst which happen to be immediately atop imperforate portions of the tube sheet between the tubes. Thus, the use of some sort of spacer-support is general in the industry, with the catalyst being spaced roughly one inch from the tube sheet. To reiterate, however, the methods by which the catalyst is supported and positioned with respect to the entrances of the aftercooler tubes are known to those skilled in the art and are outside the scope of the present invention, which is directed solely to means for enhancing the rate of cooling of the reactor effluent gases in the aftercooler tubes, with resulting reduction in the rate of chemical degradation of the formaldehyde contained in the gases being cooled.

Also outside the scope of the present invention is the design of the process aftercooler itself, except for the packing of its tubes which is, of course, central to the invention. Except for the tube packing, the aftercooler is a conventional shell-and-tube heat exchanger, oriented with its longitudinal axis substantially vertical (actually a few degrees off vertical as will be explained below) and with its upper tube sheet coupled very closely, as explained above, to the catalyst, which will be, of course, enclosed in a catalyst case the design of which will also be known to those skilled in the art and outside the scope of the present invention. Water flows through the shell of the aftercooler, preferably making a single longitudinal pass through the shell in at the bottom and out at the top. The water in the shell could be allowed to boil if desired, with steam or a mixture of steam and water being withdrawn from the upper end of the shell. However, it has been found useful in controlling the process to maintain in the shell enough pressure to keep the water in the liquid phase. Typically, water enters the bottom of the shell at about 205° C. and is withdrawn from the top of the shell at about 208° C. The withdrawn water is allowed to flash into steam, at about 17 atmospheres gauge pressure, in a separate steam flasher-separator outside the scope of the invention. The cooling water rate and/or the entering temperature of the cooling water can be manipulated as desired to control the temperature at which the cooled formaldehyde-containing gases are discharged from the bottom end of the aftercooler to be subsequently treated by conventional methods, such as absorption in water, to recover the formaldehyde in any desired commercially useful composition such as, for example, an aqueous solution of about 40% strength. Typically, the formaldehyde-containing gases are cooled to about 190° C. to 210° C. in their passage through the aftercooler.

In employing the present process improvement, the amount of gases passed through each tube in the aftercooler can be the same as in the prior-art processes using empty tubes. That is, the presence of the balls increases the actual velocity, but the nominal velocity based on empty tubes can be the same as in the prior art. This is approximately 5 to 15 feet per second, calculated on the basis of empty tube and at standard temperature, i.e., 0° C. and 1 atmosphere absolute.

The heart of the invention is, as previously explained, the employment of spherical packing in the aftercooler tubes. Of course, exact sphericity is not essential, but serious irregularities in the shape of the balls can interfere with packing the tubes and also with removing the balls from the tubes whenever this is desired. As for size of the balls, excellent results have been obtained with balls with having a diameter approximately 55% of the internal diameter of the tubes. More broadly, the ball diameter should be approximately 45% to 65% of the internal tube diameter. Obviously, of course, the ball diameter must be at least somewhat smaller than the internal tube diameter, and the ball diameter is preferably large enough that each ball either is in contact with the tube wall or else at least not separated from the tube wall by an intervening ball. This means that balls so small as to be called "beads" rather than "balls" are not preferred. In particular, excellent results have been obtained using heat exchanger tubes having an inside diameter of approximately 1 inch containing balls having a diameter of approximately 0.5 inch.

It is recommended that the balls be solid so as to minimize dead space; that is, it is desired that the gases flowing through the tubes not be allowed to be held up in stagnant pockets.

The balls should be composed of a material which is inert to formaldehyde, as measured by its failure to catalyze the conversion of formaldehyde to carbon monoxide, under the conditions of temperature and gas composition obtaining within the tubes of the aftercooler. It will be understood that absolute inertness in this regard is probably a chimera. However, a prospective new material can be evaluated for inertness by installing it in a laboratory or pilot plant-size aftercooler and comparing its inertness, as conveniently measured by the carbon monoxide content of the cooled gases exiting from it, against the performance, measured by the same index, of the aluminosilicate balls which will be discussed more fully below. In addition to the appearance of increased amounts of carbon monoxide in the cooled gas, another indication of the lack of inertness is an increase in methanol content of the cooled gases. Reversion of formaldehyde to methanol (through the reaction of formaldehyde with hydrogen which is present in the gases) has also been found to be an undesired reaction which can take place in the aftercooler. The exact cause of this reversion reaction is not known with certainty, but it is believed that it may result from the catalytic rehydrogenation of the formaldehyde in the presence of, for example, hot metal surfaces. The rapid cooling obtained by use of the present process improvment reduces the extent of this reversion reaction as compared with that obtaining in empty tubes or in the presence of packing materials such as twisted metal ribbons which are capable of catalyzing the reversion reaction if cooling in the aftercooler has not been rapid enough.

Ceramics generally are useful materials for the balls used to pack the tubes, especially aluminosilicates, and in particular the aluminosilicates containing about 30 wt % $Al_2O_3$ and about 56% $SiO_2$ having a specific gravity of about 2.4 and manufactured by the Norton Company, Chemical Process Products Division, Akron, Ohio under the trade name "Denstone 57." This material is reported to have a pore volume of 1.5% and a thermal conductivity of 8 BTU/hr/sq ft/°F./in.

The following examples are given to illustrate further the practice of the invention. It will be understood that many variations can be made therefrom within the scope of the invention.

EXAMPLE I

Operation According to the Prior Art

An integrated reactor-aftercooler was employed which comprised a substantially vertical, cylindrical shell-and-tube heat exchanger (the reaction aftercooler) containing 26 one-inch tubes having an inside diameter of 0.87 inch and 4 feet long. The tubes were fabricated from high-alloy stainless steel containing about 44% iron, 29% nickel, 20% chromium, 2% Mo, 3% Cu, 0.75% Mn, and 1% Si. Water was circulated through the shell of the aftercooler, from the bottom to the top, at a temperature of about 205° C. in the bottom of the shell and about 208° C. at the top of the shell. The water temperature varied somewhat during the course of the several runs to be described, but was broadly always in the range of about 195° C. to 215° C. Hot water withdrawn from the top of the aftercooler was allowed to flash into steam, in separate apparatus the operation of which is not relevant to the present invention. To prevent accumulation of any gas or vapor under the upper tube sheet, the heat exchanger was oriented 7° off vertical instead of being completely vertical. This allowed any accumulated gas to be swept out from under the upper tube sheet with the exiting hot water. The upper head of the aftercooler, flanged to the top of the shell, served as a reaction chamber for the catalytic oxidation-hydrogenation of methanol to produce formaldehyde, a gaseous mixture comprising methanol and molecular oxygen along with water vapor being introduced into the upper portion of this reaction chamber. Formaldehyde was a component of this feed gas mixture in those instances in which this catalyst and associated aftercooler were being used as the second stage of a two-stage methanol-oxidation system. In those instances in which it was being used as the first, or the only, stage of the methanol-oxidation reaction, the feed gases contained, of course, no formaldehyde. Details of the composition of the feed gas are outside the scope of the invention, which deals only with rapid cooling of the reactor effluent gases and not with any aspect of the control of the catalytic reaction itself; the reaction itself is conducted in accordance with known prior art techniques and need not be modified in any manner to adapt the present invention to it.

The catalyst chamber as described above contained a particulate silver-based catalyst which was supported in a thin layer on two layers of silver screen which were supported in turn by a perforated Type 316 stainless steel plate lying immediately atop the upper tube sheet of the aftercooler. The perforated plate was about ¼ inch thick. In addition to having multiple round perforations it was deeply grooved in the imperforate portions of its top face with a multiplicity of channels so as to allow transverse movement of gases along the face of the plate under the screens between adjacent perforations. The two layers of screen and the grooved plate served to keep the catalyst out of direct contact with the relatively cold aftercooler tube sheet. The layer of silver screen was approximately 0.1 inch thick. The catalyst itself normally operated at a temperature of about 550°–650° C. In 2-stage reaction systems, the second stage operates in the middle or upper end of this range, with the first stage being approximately 50° C. cooler.

Provisions were made to analyze chemically the cooled reaction product gases exiting from the bottom head of the aftercooler, the design of the bottom head being otherwise conventional and involving no special features related to the present invention. The reaction effluent gases passing through each tube of the aftercooler amounted to approximately 90 cu ft/hour calculated at 0° C. and 1 atmosphere pressure. The actual pressure was approximately 1.6 atmosphere absolute at the inlet and 1.4 atmosphere absolute at the outlet of the aftercooler. The actual temperature was approximately 600° C. immediately below the catalyst and approximately 190° C. to 240° C. at the outlet of the aftercooler.

With the reactor and aftercooler operating as just described, with the aftercooler tubes empty, and with water entering the aftercooler shell at about 202° C. and leaving the top of the shell at about 205° C., the cooled gases being discharged from the bottom end of the aftercooler tubes had a temperature of about 280° C. contained, in mole percent, approximately 17 to 19% formaldehyde, 8 to 11% hydrogen, no more than a trace of oxygen, 1.5 to 2.5% methanol, and 0.5 to 1.0% carbon monoxide during a total operating period of approximately 96 hours. Regarding the methanol and carbon monoxide contents specifically, the methanol content averaged 1.7 mole % and the carbon monoxide content averaged 0.7 mole % during this operating period.

The foregoing illustrates operating results obtained using an aftercooler operating in accordance with prior art practices, i.e., without the benefit of the present invention. Carbon monoxide in the cooled gases leaving the aftercooler is symptomatic of product degradation. Methanol may be the result of a reversion reaction in which formaldehyde recombines with hydrogen to form methanol.

EXAMPLE 2

Operation Using Heat-Transfer Enrichment with Twisted Metal Ribbons

The reactor was operated for a period of approximately 130 hours with the same reaction system as in Example 1 but with the aftercooler tubes all being filled with Type 316 stainless steel twisted metal ribbon inserts. Conditions of inlet hot gas composition, gas throughput per tube in the aftercooler, and water temperature in the aftercooler shell, were substantially identical with those obtaining during the test with empty aftercooler tubes as described above. However, the temperature of the cooled gases leaving the bottom end of the aftercooler tubes was approximately 230° C. to 250° C. whereas in the case of the empty tubes it had been approximately 270° C. to 290° C. Over a period of approximately 100 hours of operation the cooled gases leaving the aftercooler, while otherwise having substantially the same composition as the cooled gases produced by using empty tubes as described above, contained approximately 0.7 mole % to 1.0 mole % carbon monoxide and approximately 0.8 mole % to 1.2 mole % methanol. The actual average carbon monoxide content was 0.9 mole %, and the actual average methanol content was 0.9 mole %, this being over a period of approximately 20 hours.

EXAMPLE 3

Operation with Ceramic Balls for Heat Transfer Enhancement

With the same apparatus and the same reaction conditions as in the preceding Examples, the aftercooler was now operated with all of the tubes being packed with "Denstone 57" aluminosilicate ceramic balls, as more specifically described hereinabove, in place of the twisted metal ribbons. The balls which were employed were approximately 0.5 inch in diameter. Each aftercooler tube was filled with these balls, which tended naturally to assume a generally helical stacking pattern in each tube. The top of the topmost ball in each tube was approximately 0.5 inch below the top (inlet) end of the aftercooler tube containing it. The balls were held in the tubes by a metal screen clamped against the face of the lower tube sheet of the aftercooler.

The reactor and associated aftercooler were operated for a period of approximately 100 hours with the tubes being packed with the ceramic balls as just described. The inlet temperature of the hot gas entering the tubes, the inlet gas composition, and the rate of gas throughput through each of the tubes were substantially the same as during the periods of operation with empty tubes and with twisted metal inserts as described above. However, the temperature of the cooled gas being discharged from the bottom of the aftercooler was approximately 200° C. to 210° C., indicating that cooling had been enhanced as compared with the previous modes of operation even though the temperature of the water in the aftercooler shell was substantially the same as before. Over a period of approximately 75 hours of operation, the carbon monoxide content of the cooled gases ranged between 0 mole % and 0.05 mole %, averaging 0.01 mole%. The methanol content ranged between 0.6 mole % and 1.1 mole %, averaging 0.75 mole %. It will be seen that both carbon monoxide and methanol were present in a lower concentration than observed with empty tubes or with tubes containing twisted metal ribbons.

Close study of the temperature data will show that, at 200° C. to 210° C., the temperature of the cooled gases leaving the bottom of the aftercooler is extremely close to the temperature of the cooling water in the shell at the same location (about 202° C. ti 205° C. as set forth in Example 1). That is, there is little if any temperature differential between the coolant and the gases being cooled. This seeming anomaly was checked carefully, however, and the indicated temperature varified as being close to correct. It may be that an unidentified endothermal reaction takes place inside the tubes with the result that, where the presently-obtained heat transfer enhancement has already reduced the temperature to a level close to that of the coolant, a slight temperature reduction caused by such endothermal reaction can be detected through this unexpectedly close temperature differential. In any case, however, it is apparent that such endothermal reaction is either not unique to the system in which the ceramic balls are being employed or else that, if it is unique to this system, it is at any rate not a formaldehyde-decomposition reaction because the carbon monoxide content of the cooled gases produced in this example is extremely low.

The foregoing results were obtained, as can be seen, during the cooling of a reaction product gas containing very little methanol (i.e., a gas corresponding to either the second stage of a two-stage oxidation reaction system or the first and only stage of a single-stage high conversion system. The present improved cooling system is also, however, applicable to cooling the hot reaction gases being discharged from the first stage of a two-stage catalytic reaction system in which methanol is being converted to formaldehyde. The application of the invention to such a first-stage reactor is the same as has just been described above for cooling the hot effluent from the second reaction stage of a two-stage system. In both cases it will be understood, of course, that those skilled in the art wishing to adapt the present method to an existing installation may find it expedient to experiment with design details such as tube length, ball diameter, tube diameter, etc. For such applications of the invention it is broadly recommended that the aftercoolers be sized in accordance with prior-art design methods normally used with empty tubes and that the tubes then be packed with ball inserts as described herein. The cooling efficiency will be improved as compared with empty tubes, and, most important, the degree to which formaldehyde in the reactor product is degraded to methanol or carbon monoxide will be reduced. Actually, where the desideratum is the reduction of the heat-transfer surface of the aftercooler to an absolute minimum, it has been found that, when the aftercooler tubes are packed with balls as in the present Example, their length can be reduced to about half the length required when using empty tubes while still maintaining the minimal rate of formaldehyde decomposition resulting from application of the present process improvement.

The embodiments of the invention in which an exclusive property or privilege is claimed are defined as follows:

1. In a process for converting methanol to formaldehyde, which process comprises (a) continuously passing a vaporous mixture comprising methanol and molecular oxygen through a converter containing a solid catalyst, (b) continuously converting at least a portion of the methanol in said vaporous mixture to formaldehyde in the presence of said catalyst, (c) continuously withdrawing from said converter a hot gaseous reaction product comprising formaldehyde at a temperature in the range of about 290° C. to 700° C., (d) continuously cooling said hot gaseous reaction product, and (e) processing the resulting cooled reaction product to recover a formaldehyde composition therefrom, the improvement which comprises: effecting said cooling by passing said hot gaseous reaction product through an array of externally-cooled tubes filled with balls composed of an inert solid.

2. The improvement of claim 1 wherein the diameter of said balls is approximately 55% of the internal diameter of said tubes.

3. The improvement of claim 1 wherein said balls are composed of a ceramic.

4. The improvement of claim 3 wherein said ceramic is an aluminosilicate.

5. The improvement of claim 4 wherein said aluminosilicate contains about 38 wt% $Al_2O_3$ and about 56% $SiO_2$ and has a specific gravity of about 2.4.

6. The improvement of claim 3 wherein said tubes have an inside diameter of approximately 1 inch and said balls have a diameter of approximately 0.5 inch.

* * * * *